US005702941A

United States Patent [19]
Schwarz

[11] Patent Number: 5,702,941
[45] Date of Patent: Dec. 30, 1997

[54] GAS PERMEABLE BIOREACTOR AND METHOD OF USE

[75] Inventor: Ray P. Schwarz, Friendswood, Tex.

[73] Assignee: Synthecon, Inc., Houston, Tex.

[21] Appl. No.: 602,702

[22] Filed: Feb. 16, 1996

Related U.S. Application Data

[63] Continuation-in-part of Ser. No. 416,908, Apr. 21, 1995, which is a continuation-in-part of Ser. No. 118,512, Sep. 9, 1993, Pat. No. 5,437,998.

[51] Int. Cl.[6] .................. C12N 5/02; C12M 3/00
[52] U.S. Cl. .............. 435/243; 435/297.1; 435/298.2; 435/818
[58] Field of Search ............ 435/240.25, 240.26, 435/240.54, 297.1, 298.2, 300.1, 818

[56] References Cited

U.S. PATENT DOCUMENTS 5,330,908   7/1994   Spaulding .................. 435/240.24

*Primary Examiner*—David A. Redding
*Attorney, Agent, or Firm*—Wendy K. Buskop; Chamberlain, Hrdlicka et al.

[57] ABSTRACT

This invention relates to an apparatus and method of use for a new simply constructed bioreactor made at least partially of gas permeable materials. The bioreactor is useful for culturing cells and tissues in suspension as well as attached to the inside surface of the bioreactor in a liquid nutrient medium with minimum turbulence. The bioreactor may include ports for easy access to the vessel culture, allowing the growth substrate to be varied for optimum performance.

8 Claims, 4 Drawing Sheets

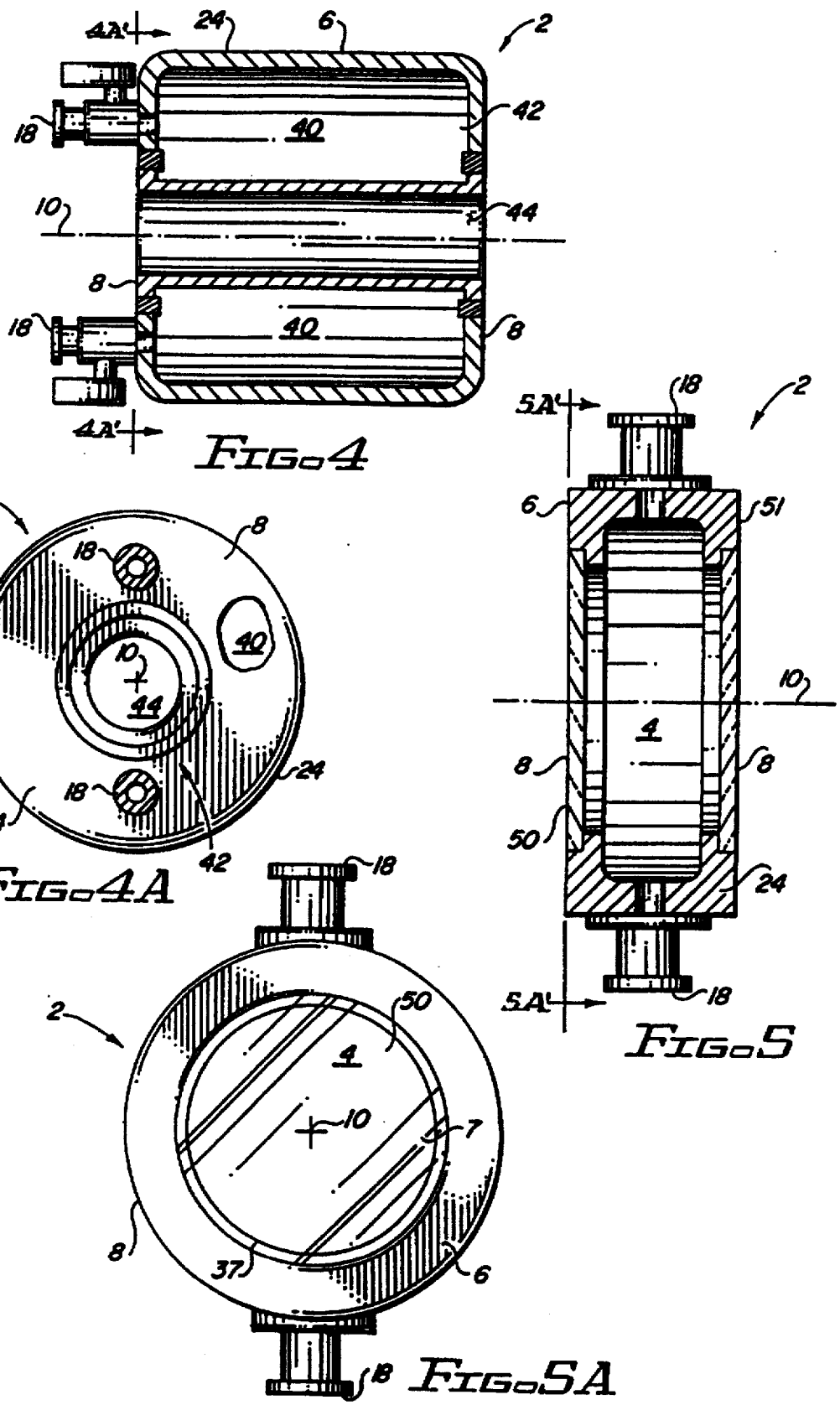

GAS PERMEABLE BIOREACTOR AND METHOD OF USE

SPECIFICATION

This application is a continuation-in-part of application Ser. No. 08/416,908, filed under 35 USC § 371 on Apr. 21, 1995 from PCT application Ser. No. PCT/US94/10126, filed Sep. 9, 1994 and claiming a priority as a continuation-in-part from U.S. application Ser. No. 08/118,512, filed Sep. 9, 1993, now U.S. Pat. No. 5,437,998.

BACKGROUND

This invention relates to an apparatus and method of use for a new simply constructed bioreactor made at least partially of gas permeable materials. The bioreactor is useful for culturing cells and tissues in suspension in a liquid nutrient medium with minimum turbulence. The bioreactor may include ports for easy access to the vessel culture, allowing the growth substrate to be varied for optimum performance.

A primary use is in research where large numbers of cells are grown to refine the minute quantities of an active material (e.g., proteins) that the cells might secrete. Another use of bioreactors is the scale-up of laboratory cell culture processes for commercial purposes to mass produce the active proteins made by genetically engineered cells. Because of the need to culture mammalian cells in the laboratory in large quantities, bioreactors have become an important tool in research and production of cells that produce active proteins.

A current problem in tissue culture technology is the unavailability of an inexpensive bioreactor for the in vitro cultivation of cells and explants that allows easy access to the materials contained in the vessel. Several devices presently on the market have been used with considerable success, but each has its limitations which restrict usefulness and versatility.

Cell culturing devices range upward in complexity from the petri dish, to plastic flasks, to sophisticated computer controlled bioreactors. In the past, manufacturers have promoted various technologies to culture cells in the laboratory. Simple adaptations of fermentors (stirred tanks) used for the culture of bacteria were marketed previously as the answer to culturing delicate mammalian cells. One of the principal factors limiting the performance of these systems is their inability to minimize turbulence due to stirring, i.e., shear due to fluid flow, and hence preventing free form association of cells in three dimensions.

Another utilized technology is microcarrier cell culture, which involves the use of substrate particles, generally collagen-coated beads, to culture anchorage dependent cells. Bioreactors for microcarrier or suspension cells must suspend the cells and substrate in a fluid medium. In the past, this generally was done with an impeller in a stirred tank. Oxygen ($O_2$) was provided by sparging (i.e., bubbling) air through the liquid medium. Both the impeller and the bubbling air, unfortunately, create turbulence.

An improved method of suspending particles (cells and their substrate) that minimizes fluid turbulence, while at the same time providing the required oxygen transfer, is needed to improve the performance of bioreactors. It is an object of the present invention to provide both an apparatus and a method for culturing cells that overcomes the technological limitations of prior bioreactor systems.

SUMMARY

The present invention is directed to a new class of bioreactor for cell culture and a method for use of the bioreactor, whereby the preferred embodiment of the apparatus is a gas permeable bioreactor comprising a tubular vessel with walls constructed at least partially of a gas permeable material. The tubular vessel has closed ends, a substantially horizontal longitudinal central axis, and one or more vessel access ports for transferring materials into and out of the tubular vessel. Means is provided for rotating the vessel about its horizontal longitudinal central axis.

In another preferred embodiment of the apparatus of this invention, the gas permeable bioreactor is a tubular vessel with walls constructed at least partially of a gas permeable material. It has closed ends, a substantially horizontal longitudinal central axis, and is constructed of two sliding members. A first sliding member fits slidably into a second sliding member, forming a liquid tight seal therebetween. The vessel also has means for rotating it about its horizontal longitudinal central axis. One or more access ports are provided on the vessel for transferring materials into and out of said vessel.

An alternative embodiment of the bioreactor of the present invention is an annular vessel with walls constructed at least partially of a gas permeable material. The annular vessel has closed ends, which leaves the central portion of the vessel open. The annular vessel rotates around a substantially horizontal longitudinal central axis and has means for rotating the vessel. One or more access ports are provided for transferring materials into and out of the vessel.

The bioreactor of the present invention is constructed at least partially of a gas permeable material, such as, but not limited to, silicone rubber, polytetrafluoroethylene (also known as Teflon®, a registered trademark of DuPont), polyethylene, porous polytetrafluoroethylene, other porous plastics, porous plastics coated with a hydrophobic material, mixtures of silicone rubber with other plastics, or silicone rubber coated cloth. In one preferred embodiment of the present invention the vessel is formed of injection molded gas permeable plastic.

It is an object of the present invention to provide a bioreactor vessel that uses only horizontal rotation (clinostatic suspension) to suspend particles in a culture vessel. This is an advantage over the prior art, which required stirring or mixing for particle suspension and oxygenation. The bioreactor of this invention, in contrast, provides a very low turbulence regime. The present invention also overcomes the prior art need for air injection into the bioreactor vessel. The use of air injection is not excluded from the present invention, however. The gas permeable material of which the bioreactor of this invention is constructed provides this advantage by allowing $O_2$ to diffuse through the vessel walls and into the cell culture media in the vessel chamber. Correspondingly, carbon dioxide ($CO_2$) diffuses through the walls and out of the vessel. Clinostatic suspension combined with oxygenation by diffusion merges ideal properties for a high performance bioreactor vessel.

It is another object of the present invention to provide a bioreactor vessel that is disposable. Due to the present bioreactor's simple design and construction, it can be easily and economically manufactured. The resulting bioreactor is consequently affordable, disposable, and may be mass produced. In situations where minimization of contamination is necessary (e.g., AIDS or human tissue research), disposability of the bioreactor is a particular advantage. While the bioreactor may be produced in a wide variety of sizes, its simple construction provides the advantage of allowing bioreactors to be made smaller than previously possible. The smaller sizes are helpful in research laboratories, in particular. Moreover, the embodiment of the bioreactor with two slidably interconnected members may be adjusted to provide the exact size bioreactor needed.

Another aspect of the present invention is a method for growing cells in a gas permeable bioreactor. The method involves filling a bioreactor constructed at least partially of a gas permeable material with a liquid culture medium and cells; suspending said cells, without appreciable mixing, in the cell media by rotating the bioreactor about its horizontal longitudinal central axis at a rate that suspends the cells in the liquid culture medium. The rotation is continued for a time period to permit desired cell growth. An alternative embodiment of the method of this invention includes adding a growth substrate, such as substrate particles or tissue explants, to the bioreactor with the culture medium and cells.

Still other objects, features and advantages of the present invention will be apparent from the following description of the preferred embodiments given for the purpose of disclosure and taken in conjunction with the accompanying drawings.

In a further embodiment of the bioreactor of the present invention, a means is provided to trap gas bubbles which are present in the fluid medium. The trapped gas bubbles are retained away from the cell culture chamber, thus further minimizing turbulence which inhibits or prevents cell growth.

BRIEF DESCRIPTION OF DRAWINGS

FIG. 4 is a cross-sectional side view of an alternative embodiment of the bioreactor of the present invention which has an annular tubular shape.

FIG. 4A is an end view of the embodiment of the annular tubular bioreactor of FIG. 4 taken along the line 4A'—4A'.

FIG. 5 is a cross-sectional side view of another preferred embodiment of the bioreactor with clear microscope viewports on each end of the vessel.

FIG. 5A is an end view of the embodiment of the tubular bioreactor of FIG. 5 taken along the line 5A'—5A'.

DETAILED DESCRIPTION OF THE PREFERRED EMBODIMENTS

Like numbered apparatus elements in FIGS. 1–11 are the same.

Figure 1:
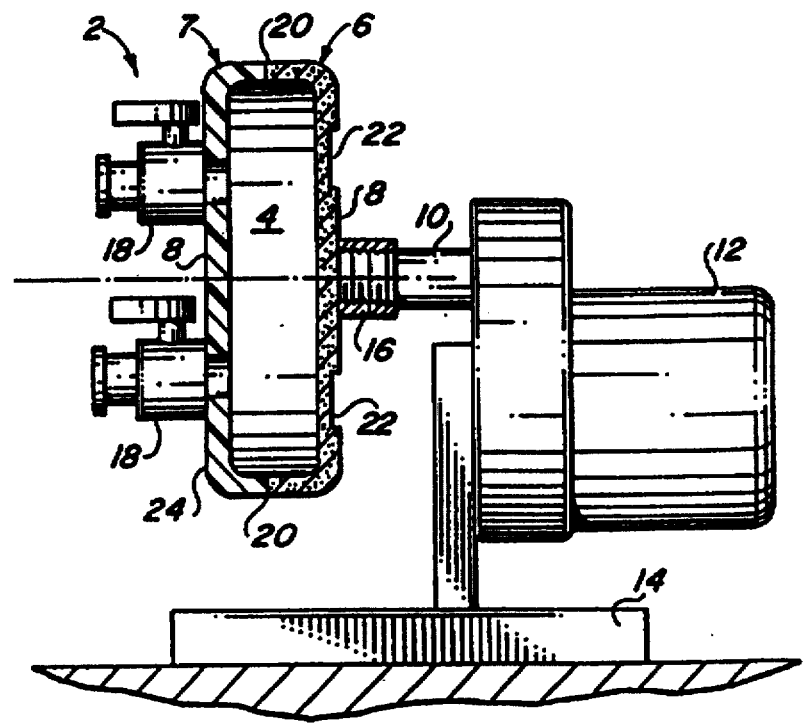
FIG. 1 is a partially cross-sectional side view of a preferred embodiment of the gas permeable bioreactor of the present invention showing attachment to a motor assembly unit for rotation purposes and showing a cross-section of the bioreactor vessel.

Referring to the drawings, FIG. 1 is a cross-sectional side view of a preferred embodiment of the gas permeable bioreactor of the present invention showing a motor assembly unit for rotation purposes. In the preferred embodiment of the invention, the bioreactor 2 is made of a tubular vessel 4 with outer walls 24 constructed at least partially of a gas permeable material 6 defining a vessel chamber. The outer walls 24 themselves may be constructed of the gas permeable material 6 or the material 6 may be made a part of the outer walls 24 in the same manner as the microscope viewports 50 discussed below. The vessel 4 has closed ends 8 and a substantially horizontal longitudinal central axis 10. One or more vessel access ports 18 are provided for transferring materials into and out of the vessel 4. The vessel 4 in one preferred embodiment is constructed such that half of it is comprised of gas permeable material 6 and the remaining portion is made of nonpermeable material 7.

The gas permeable materials 6 commonly available are opaque. Thus, using nonpermeable material 7 for part of the bioreactor 2 may provide an advantage in allowing visual inspection of the vessel chamber. To further enhance oxygen absorption into the vessel chamber, depressions 22 may be formed in the outer walls 24 in areas where there is gas permeable material 6. The thinner the outer wall 24, the less distance the oxygen must travel before entering the vessel chamber. The gas permeable material 6 used to make the bioreactor 2 preferably is a porous, hydrophobic material. It may be a porous nonhydrophobic material coated on one side with silicone rubber or some other hydrophobic material to achieve gas permeability. However, if the pore size of the porous material is one micron or less, a coating is not preferred. In the preferred embodiment, the porous material used is a "foamed" plastic, which is a hardened porous plastic. This porous plastic is available commercially in a variety of pore sizes from companies such as Porex Technologies (located in Fairburn, Ga.). For instance, Porex manufactures products in porous polytetrafluoroethylene and polyethylene that are suitable for use in this invention.

Any nonpermeable material 7 used to construct the outer walls 24 preferably is a transparent, nontoxic, biocompatible material such as clear plastic. Most preferably the clear material is polycarbonate (also known as Lexan®, a registered trademark of General Electric). The bioreactor 2, furthermore, may be made of a variety of materials: silicone rubber, polytetrafluoroethylene, polyethylene, porous plastic, porous plastic coated with a hydrophobic material, mixtures of silicone rubber with other plastics, and silicone rubber coated cloth. Preferably, the bioreactor 2 is constructed of porous plastic coated with a hydrophobic material on the interior surface. Most preferably, the vessel 4 is made of porous hydrophobic teflon. The vessel 4 may also be formed out of injection molded plastic. When injection molded plastic is used, the molded pieces of the vessel 4 may be welded, glued; or mechanically attached together. Preferably, the vessel is made in two pieces which are welded, glued, or mechanically attached together around a circumferential seam 20, as shown in FIG. 1. Other construction methods may be used, however, such that the vessel 4 may be formed of one piece of molded plastic, thus eliminating the circumferential seam 20. The bioreactor 2 is constructed at least partially of a gas permeable material 6, and the percentage of the vessel made of gas permeable material may vary from about 5% to about 100%. In one preferred embodiment of the bioreactor 2, the vessel 4 is constructed with a first half comprised of gas permeable material 6 and a second half comprised of a non-gas permeable material 7.

The vessel 4 may be made in any size, so long as the surface area to volume ratio of the vessel 4 is large enough to allow adequate gas transfer through the outer walls 24 to the cell culture in the vessel 4. As a vessel 4 gets larger (by expanding all dimensions proportionally) the volume increases as the cube of its dimensions, whereas the surface area increases as the square of its dimensions. Once a certain size is reached, the reduced surface area per volume will hinder adequate gas transfer. This can be avoided, however, by scaling up the size in one dimension only. For instance, the length of the vessel may be increased but not the diameter, or the diameter may be increased but not the length. For vessels of a size of 500 ml or less, the dimensions of the vessel 4 are not critical.

Additionally, the dimensions and shapes of the vessels 4 are use dependent. The type of cells being grown and the use of substrate carriers affects gas transfer. When the suspension cells are lightweight, they cause little rulling and oxygen must travel further from the outer wall 24 to the cells. When larger cell colonies are grown on substrate carriers, mixing results such that less gas transfer is required for oxygenation of the cells. The acceptable variations of the dimensions are endless, but those skilled in the art will be able to adjust the dimensions to suit the particular application, while still providing adequate $O_2$ transfer.

In the preferred embodiment of the invention, the volumetric size of the vessel chamber is preferably in the range of about 1 ml to about 500 ml. The diameter of the vessel 4 preferably is in the range of about 2.54 cm (1 inch) to about 15.24 cm (6 inches). The most preferred range of diameters is in the range of about 7.62 cm (3 inches) to about 15.24 cm (6 inches).

The width of the bioreactor 2, due to the permeability of the outer walls 24, may be doubled relative to widths in prior art designs, since gas can be transferred from all vessel surfaces. For cells in free suspension (very small particles which do not settle quickly) the preferred chamber width is about 0.635 cm (0.25 inch), but may be in the range of about 0.318 cm (0.125 inch) to about 2.54 cm (1 inch). While the volume of the vessel chamber may be any size, it should be kept in mind that the bioreactor 2 produces at least 10 to 20 million cells per milliliter. Thus, a vessel 4 of 2.0 liters would allow growth of approximately 20 billion cells. An advantage of this productivity, is that smaller vessels 4 may be used than ever before.

A preferred means for rotation is a motor assembly 12 as shown in FIG. 1. The motor assembly 12 sits on a mounting base 14 and has means 16 for attachment to the vessel 4. Preferably, the means for attachment 16 comprises threadably connecting the vessel 4 to the motor assembly 12 through screw threads on the drive shaft corresponding to screw threads on the vessel 4. Preferably, these screw threads are in a direction such that inadvertent loosening of the vessel 4 from the motor assembly 12 due to the movement of rotation is avoided. In addition, a lock nut or similar device may be provided on the drive shall to prevent unscrewing. In the preferred embodiment, a 1.59 cm (0.625 inch) threaded shaft coupling is used, but this may be varied to coordinate with the size of the bioreactor 2.

Figure 9:
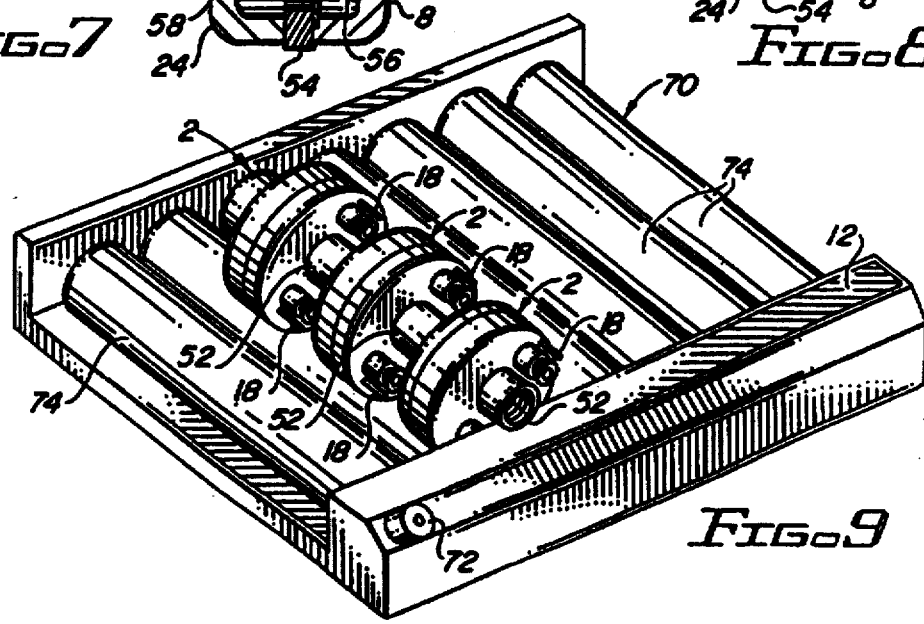
FIG. 9 is a perspective view of a preferred embodiment of a roller mechanism used to rotate one or more bioreactors, showing three bioreactors attached end-to-end and rotating thereon.

The means for rotation in one preferred embodiment is a roller mechanism 70 as shown in FIG. 9. The roller mechanism 70 has multiple rollers 74 stretched longitudinally in a horizontal plane which rotate simultaneously to correspondingly rotate any bioreactor 2 laid on the roller mechanism 70. Such roller mechanisms 70 are commercially available. The bioreactor 2 of the present invention may be rotated on a roller mechanism 70 such as the ones produced by Stoval Life Science, Inc. Stoval manufactures compact, nondedicated roller units which perform multiple functions in the biological research laboratory. It operates on benchtops, in high humidity and carbon dioxide incubators, high temperature ovens (to 65° C.), and in refrigerated units (0° C.). The roller mechanism 70 has speed control operated by a speed control knob 72. Other roller mechanisms 70, of course, may be utilized as will be commonly known to those skilled in the art.

The preferred speed of rotation is in the range of about 2.0 revolutions per minute (rpm) to about 40 rpm and is largely dependent on the specific bioreactor and what is being cultured. For example, for a bioreactor of about 7.62 to 12.7 cm (3 to 5 inches) in diameter, with a width of about 0.635 cm (0.25 inch), growing BHK-21 cells in a microcarrier culture, the preferred speed of rotation is about 24 rpm. Speed must be adjusted to balance the gravitational force against the centrifugal force caused by the rotation. For vessels of up to about 6.35 cm (5 inches) in diameter, the rotational speed may range from about 2 rpm for single cells in suspension, up to about 40 rpm for large particles grown on microcarrier substrates.

As shown in FIG. 1, the vessel access ports 18 provide access to the bioreactor 2 for input of medium and cells and for removal of old medium from the vessel 4. This is easily done through the vessel access ports 18, which are also referred to as valves or syringe ports. In the preferred embodiment, the vessel access ports 18 are constructed of valves with syringe ports. The valves preferably are plastic, but may be made of metal or any other material which is non-toxic and is hard enough for machining into an access port. The carbon dioxide produced by the cells when they use oxygen and metabolize sugar leaves the vessel chamber primarily by traveling out through the gas permeable outer wall 24 of the vessel 4.

Another advantage of the new gas permeable bioreactor 2 is that air filters for the $O_2$ source are unnecessary, as previously required. The prior art bioreactors required an air filter to protect the air pump valves from dirt. The bioreactor 2 of the present invention relies on the rotation of the vessel 4 to circulate fresh air over its surface.

Figures 7, 8:
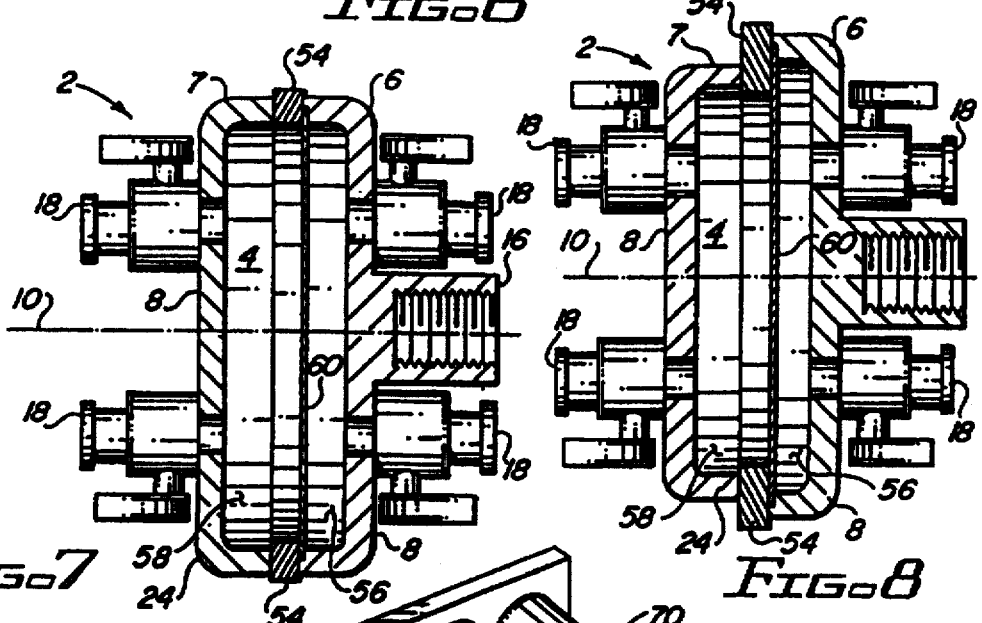
FIG. 7 is an alternative embodiment of the gas permeable bioreactor with an internal membrane dividing the vessel into two chambers, one for cell culture and one for exchanging cell medium without disturbing the cells in the other chamber.
FIG. 8 is an alternate embodiment of the gas permeable bioreactor where the inside diameter of the chamber designed for exchanging cell medium has been enlarged to enable the chamber to further function as a trap for gas bubbles.

In an alternative embodiment of the bioreactor 2, as shown in FIG. 7, a permeable membrane 60 is inserted into the vessel 4 in a plane substantially perpendicular to the horizontal axis 10 to separate the vessel 4 into two chambers: a cell growth chamber 58 and a reservoir chamber 56. It should be noted, however, that the two chambers 58, 56 are functionally interchangeable, i.e., either one may be used for cell growth. The cell growth chamber 58 preferably is used for cell culture. The reservoir chamber 56 may be filled and refilled with fresh medium without disturbing the cell culture in the cell growth chamber 58. The membrane 60 has a porosity that allows medium and metabolic waste to travel through it, but cells and substrates are too large to do so.

Thus, this embodiment of the invention allows greater freedom in replacing the cell medium, particularly when the cell culture is producing large amounts of waste metabolites. In some past systems, it was necessary to centrifuge the cell culture to separate the cells from the medium in order to accomplish a change of the medium. This embodiment of the invention avoids the need to centrifuge the cell culture suspension.

In this embodiment of the invention, four vessel access ports 18 are used to allow access to the contents of the vessel 4 on each side of the membrane 60. Furthermore, a seam bracket 54 between two pieces of the vessel 4 may be used to attach the membrane 60 across the vessel 4. Alternatively, the membrane may be glued, welded, or mechanically attached between the pieces of the vessel 4.

Another feature of the present invention is a microscope viewport 50 which may be incorporated into the outer walls 24. FIGS. 5 and 5A portray a bioreactor 2 of the present invention made entirely of gas permeable material 6, except for microscope viewports 50 which are incorporated on each end 8 of the vessel 4. The viewports 50 may be glued, welded, or mechanically attached to the ends 8. Moreover, as shown in FIG. 5., the ends 8 may be formed to provide shoulders 51 for the viewports 50 to rest against and be attached to. Preferably, two microscope viewports 50 are incorporated into the vessel walls 4 opposite to each other, so that the microscope will have a clear viewing path through the vessel 4. FIG. 5A is an end view of the bioreactor 2 of FIG. 5 taken along the line 5A'—5A'.

Figure 6:
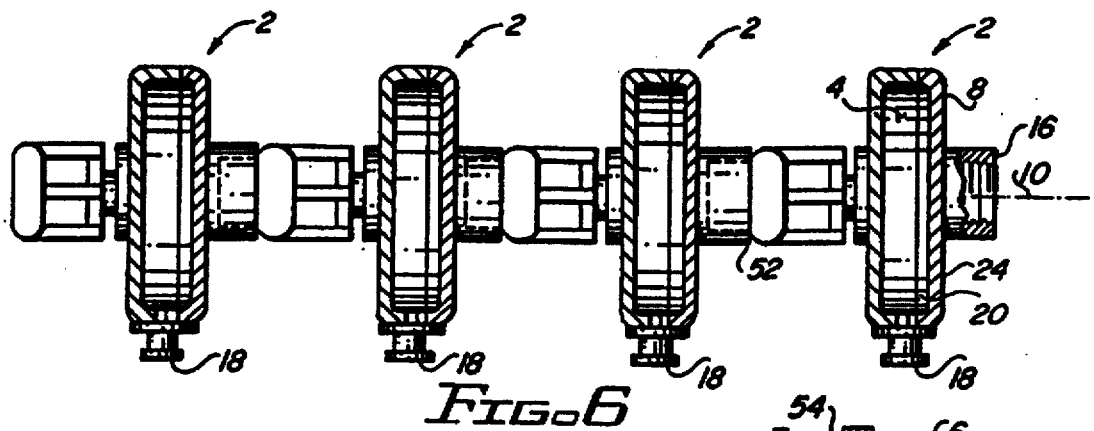
FIG. 6 is a cross-sectional partially expanded side view of an alternative embodiment of the bioreactor where multiple bioreactors are attached to each other end to end.

As shown in FIG. 6, the bioreactor 2 of the present invention may also be constructed with means 52 on one or both ends 8 for attaching one vessel 4 to an additional vessel 4, thereby creating a chain of bioreactors 2. When a chain of bioreactors 2 is formed in this manner, the chain may be attached to a means for rotation at one of its ends 8. If a motor assembly is used for rotation of the chain of bioreactors 2, the vessel access port 18 may be located on the circumferential perimeter of the vessel 4 for easier access. However, if the chain of bioreactors 2 is to be rotated on a roller mechanism 70, the vessel access ports 18 should be located on the vessel 4 ends 8.

Figure 2:
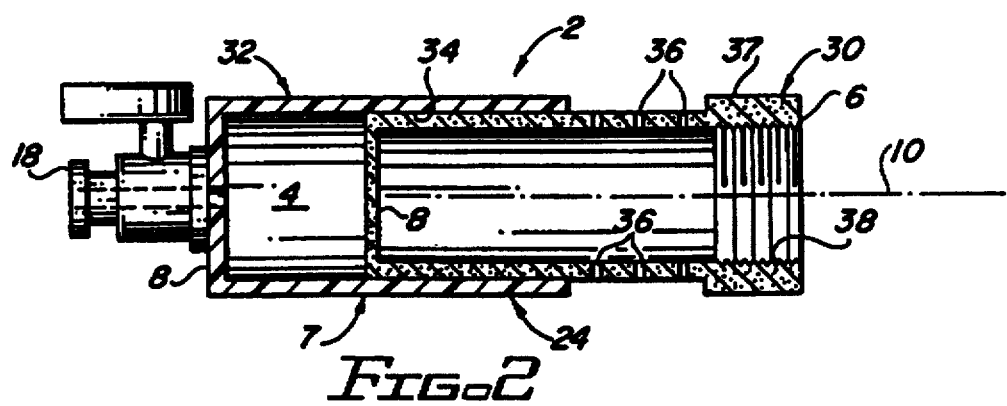
FIG. 2 is a cross-sectional side view of another preferred embodiment of the bioreactor having two slidably interconnected members to provide a variable volume vessel. The bioreactor is shown in the open position.
Figure 3:
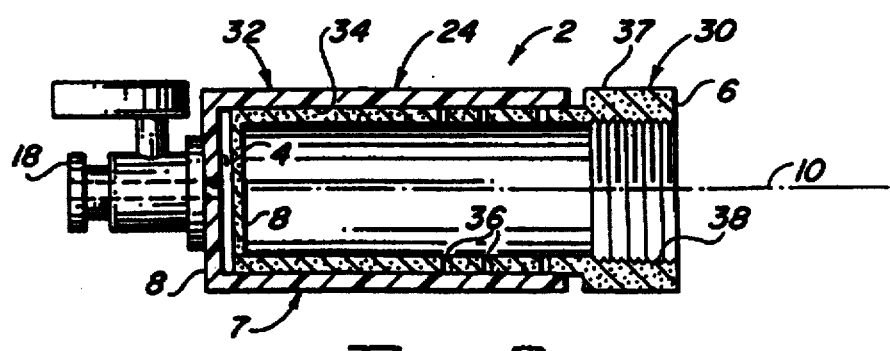
FIG. 3 is a cross-sectional side view of the bioreactor shown in FIG. 2 in the closed position.

The present invention also includes a bioreactor 2 with a variable volume, as shown in FIGS. 2 and 3. In this embodiment of the bioreactor 2, the bioreactor 2 is comprised of a vessel 4 constructed at least partially of a gas permeable material 6. The vessel 4 has closed ends 8 and a substantially horizontal longitudinal central axis 10 around which it rotates. The vessel 4, furthermore, has two slidably interconnected members 30, 32, wherein a first member 30 fits slidably into a second member 32, forming a liquid tight seal 34 therebetween and providing a variable volume vessel 4. The bioreactor 2 has means for rotating the vessel 4 about its substantially horizontal longitudinal central axis 10. One or more vessel access ports 18 are provided for transferring materials into and out of the vessel 4.

Where the variable volume embodiment of the bioreactor 2 is rotated by attachment to a motor assembly that occludes the open end of the first member 30, air ports 36 may be added to the first member 30 to assist with $O_2$ transfer into the vessel chamber. In addition, a shoulder 37 on the first slidably interconnected member 30 may provide a resting place for the drive shaft to rest against when threadably connected to the screw threads in the end 8 of the member 30.

This embodiment of the bioreactor may be made of the same materials as described above for the other embodiments of the bioreactor 2. Preferably, the first tubular member 30 is formed of gas permeable material 6, and the second tubular member 32 is formed of a clear, non-toxic, biocompatible material.

The same means for rotating the tubular vessel 4 may be used as described above, and most preferably by the motor assembly 12 shown in FIG. 1. One or more vessel access ports 18 for transferring materials into and out of the tubular vessel 4 are located on the end 8 of the vessel 4. The volume of the vessel 4 may be varied by the relative movement of the first and second members 30, 32. The vessel members 30, 32 behave as a sliding plunger assembly, similar to a syringe. The seal 34 on the first slidable interconnected member 30 preferably is a rubber gasket, such as an O ring, which may be fitted into a depression around the circumference of the first member 30 near its end 8. The opposing end of the first member 30 is open to allow air or other gases to move freely inside the member 30.

An alternative embodiment of the bioreactor of the present invention, as shown in FIGS. 4 and 4A, comprises an annular tubular vessel 40 with outer walls 24 constructed at least partially of a gas permeable material 6. It is constructed similarly to the embodiments of the invention described above and varies primarily in its shape. Annular is defined herein to include annular, toroidal, and other substantially symmetrical ring-like shaped vessels 40. The annular vessel 4 has closed ends 8 and a substantially horizontal longitudinal central axis 10. The central portion 44 of the vessel 40, consequently, is left open, allowing air to flow over the central portion 44 of the vessel 40. FIG. 4A is an end view of the embodiment of the annular tubular bioreactor of FIG. 4 taken along line 4A'—4A'.

Means for rotating the annular vessel 40 about its substantially horizontal longitudinal central axis 10 is preferably a motor assembly 12 as depicted in FIG. 1. Screw threads may be provided in the walls of one end of the central portion 44 of the vessel 40. Other means for rotating the vessel may be used, however, as described above. Two vessel access ports 18, preferably are provided on one end 8 of the vessel 40 to allow cells, medium, and other materials to be transferred into and out of the vessel 40.

Another aspect of the present invention is a method for growing cells in a gas permeable bioreactor 2 comprising filling a bioreactor 2 constructed at least partially of a gas permeable material 6 with a liquid culture medium and cells; suspending the cells, without appreciable mixing, in the cell medium by rotating the bioreactor 2 about its substantially horizontal longitudinal central axis at a rate that suspends the cells in the liquid culture medium; and continuing rotation of the bioreactor 2 for a time period that permits a desired cell growth.

Referring again to FIG. 1, the bioreactor 2, after sterilization, is filled with a liquid culture medium, such as those commonly known in the art, and cells. If desired, substrate particles may also be added. One preferred microcarrier substrate is collagen coated beads, but numerous types of substrate particles may be used and are known by those skilled in the art. Alternatively, the substrate particles may be pieces of tissue explant. Tissue explant may be diced and added to the culture medium as a substrate upon which cells grow. In addition, tissue explant may be added to a cell culture medium without the addition of other cells. Then, the explant is cultured for further cell growth. In this situation, the tissue explant takes the place functionally of both the cells and the substrate.

Once the vessel 4 is completely filled with medium and any other materials, such that no air spaces exist in the vessel, the cells. (or tissue explant if it is cultured instead) are suspended in the bioreactor 2 without any appreciable mixing by rotating the bioreactor 2 about its horizontal longitudinal central axis 10 at a rate that suspends the cells in the liquid culture medium. The appropriate rate of rotation is discussed above.

Rotation of the vessel 4 preferably takes place in the presence of an oxygen containing gas mixture with about 5% carbon dioxide. In the preferred method, the gas mixture is air. In addition, the bioreactor 2 is preferably rotated within an incubator to control the temperature of the vessel 4 culture. The temperature preferably ranges from about 35° C. to about 40° C. for mammalian cells. For any cell, of course, the temperature preferably is maintained at a level that permits cell growth. The rotation of the vessel is continued until the desired amount of cell growth occurs.

During rotation, the oxygen containing gas mixture diffuses through the permeable vessel 4 outer walls 24 and into the liquid culture medium in the chamber. Carbon dioxide produced by cellular metabolism diffuses through the medium and the outer walls 24 and is thus eliminated from the chamber. Moreover, the vessel access ports 18 allow the medium in the vessel 4 to be exchanged regularly, if desired. In cases where cells are cultured over longer periods of time, exchanging used culture medium for fresh culture medium becomes more important. Once desired cell growth is obtained, the vessel 4 may be detached from the means for rotation and the cells culture medium may be decanted from the vessel 4 for harvesting of the cells.

The method of the present invention may also be utilized with other embodiments of the bioreactor 2 of the present invention.

In an alternative embodiment of the bioreactor 2, a means is provided for trapping gas bubbles away from the cell growth. In a preferred embodiment, shown in FIG. 8, the vessel 4 has walls constructed at least partially of a gas permeable material, an inner surface, closed ends 8 and a substantially longitudinal central axis 10. A permeable membrane 60 is positioned in the vessel to provide a cell growth chamber 58 and a reservoir chamber 56. The cell growth chamber 58 has an inside surface, an inside diameter and a substantially longitudinal axis. The reservoir chamber 56 has an inside surface, an inside diameter larger than the inside diameter of the cell growth chamber 58 and a substantially longitudinal axis contiguous with the substantially longitudinal axis of the cell growth chamber 58. The reservoir chamber 56 may be filled and refilled with fresh medium without disturbing the cell culture in the cell growth chamber 58. The membrane 60 has a porosity that allows medium, gas bubbles and metabolic waste to travel through it, but cells and substrates are too large to do so. Gas bubbles which pass through the membrane migrate to the gas entrapment zone at the top of the reservoir chamber 56. Thus, this embodiment of the invention traps gas bubbles away from the cell growth chamber, minimizing turbulence in the cell growth chamber 58 and allowing free form association for cell growth.

The preferred variance in the inside diameter between the cell growth chamber 58 and the reservoir chamber 56 of the vessel 4 is in the range of about 5 percent to 10 percent. During rotation of the vessel, gas bubbles trapped in the liquid medium tend to migrate to the highest point. The gas bubbles will migrate to the top of the larger inside diameter reservoir chamber 56, where they become trapped within the entrapment zone.

In the embodiment of the invention shown in FIG. 8, four vessel access ports 18 are used to allow access to the contents of the vessel 4 on each side of the membrane 60. Furthermore, a seam bracket 54 between two pieces of the vessel 4 may be used to attach the membrane 60 across the vessel 4. Alternatively, membrane 60 may be glued, welded, or mechanically attached to vessel 4.

This embodiment of the present invention may also feature a microscope viewport 50 which may be incorporated into the vessel walls 24 as described above for other embodiments of the bioreactor 2. Means may also be provided for attaching one vessel 4 to an additional vessel 4, thereby creating a chain of bioreactors 2, as described above.

This embodiment of the bioreactor may be made of the same materials as described above for other embodiments of the bioreactor 2. Further, the same means for rotating vessel 4 may be used as described above.

Rotation of the vessel 4 may take place by rotating the vessel about the substantially longitudinal central axis in a substantially horizontal plane. Rotation of the vessel 4 may also take place by rotating the vessel about the substantially longitudinal axis in a plane inclined no more than 10 degrees from a substantially horizontal plane. When tilted rotation is used preferably the cell growth region is on the lower end of the inclined plane, while the reservoir region is on the upper end of the inclined plane.

Another aspect of the present invention is a method for growing cells in a gas permeable bioreactor comprising filling a vessel 4 with walls constructed at least partially of a gas permeable material, a permeable membrane 60 positioned to provide a cell growth chamber 58 and a reservoir chamber 56 in the vessel 4, and a means for entrapping gas bubbles away from the cell growth chamber 58, with a liquid culture medium and cells; suspending the cells in the liquid culture medium, without appreciable mixing of the liquid medium in cell growth chamber 58, by rotating the bioreactor about its substantially longitudinal central axis at a rate that suspends the cells in the liquid culture medium; trapping gas bubbles contained in the liquid growth medium in the reservoir chamber 56; and continuing rotation of the bioreactor for a time period that permits cell growth.

Referring again to FIG. 8, the bioreactor 2 is may be filled as described above. Further, tissue explant may be added as described above.

The appropriate rate for rotation is described above. Rotation of the vessel 4 may take place by rotating the vessel about the substantially longitudinal central axis in a substantially horizontal plane or by rotating the vessel 4 about the substantially longitudinal axis in a plane inclined no more than 10 degrees from a substantially horizontal plane. When tilted rotation is used, preferably the cell growth region is on the lower end of the inclined plane, while the reservoir region is on the upper end of the inclined plane. As the bioreactor 2 rotates, gas bubbles contained in the liquid medium tend to rise to the top of the vessel. As the gas bubbles reach the topmost region of the reservoir chamber 56, the gas bubbles become entrapped away from the cell growth chamber.

In an alternative embodiment, the bioreactor 2 is made of a tubular vessel 4 with outer walls 24 constructed at least partially of a gas permeable material 6 defining a vessel chamber. The outer walls 24 have an inner surface 84 and an outer surface. The inner surface 84 of the vessel 4 has a means for attaching cells such as collagen or plasma. The outer walls 24 themselves may be constructed of the gas permeable material 6 or the material 6 may be made a part of the outer walls 24 in the same manner as the microscope viewports 50 discussed above. The vessel 4 has closed ends 8 and a substantially horizontal longitudinal central axis 10. One or more vessel access ports 18 are provided for transferring materials into and out of the vessel 4. The vessel 4 in one preferred embodiment is constructed such that half of it is comprised-of gas permeable material 6 and the remaining portion is made of nonpermeable material 7. The vessel 4 preferably has rotatable connecting means, such as a rotatable coupling, attached to each vessel access port 18. A rotatable coupling attached to the vessel access port 18, allows the user to provide a constant flow of materials into and out of the vessel 4 while the vessel 4 is in motion. The materials injected into the vessel 4 can be liquid medium, oxygenated liquids, and waste products may be removed while the vessel 4 is rotating.

Figure 10:
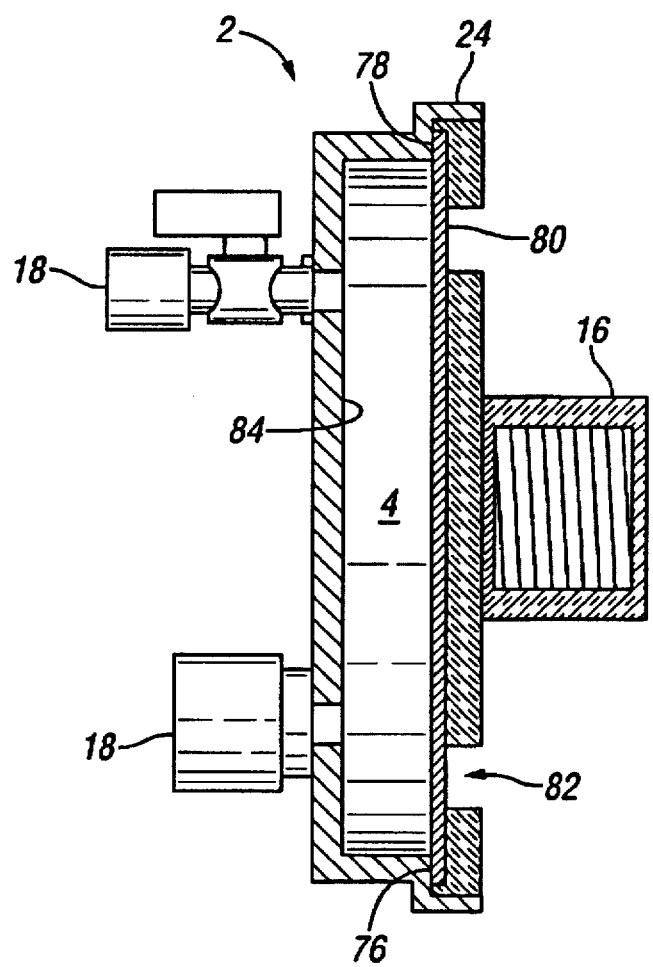
FIG. 10 is a perspective view of a preferred embodiment of the bioreactor where the outer wall has openings and forms a groove within the outer walls.
Figure 11:
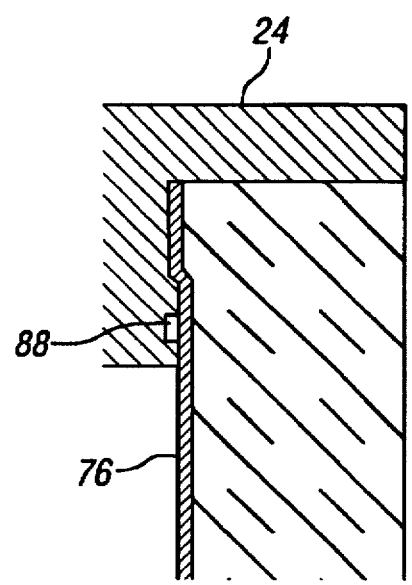
FIG. 11 is an exploded view of the bioreactor where one of the outer walls defines a groove.

Alternatively, at least one outer wall has a plurality of openings 82 that are circular and/or slotted and at least one outer wall can forming a groove 88 therein as shown in FIGS. 10 and 11. The groove 88 extends circumferentially about the gas permeable bioreactor. The gas permeable membrane has a first side and a second side and is sealably positioned within the outer walls adjacent to the groove 88.

In an alternative embodiment there is provided, a method for culturing cells in a bioreactor 2 to produce in vitro multi-cellular, three dimensional assemblies of predominately living mammalian cells attached to the inside surface of the bioreactor 2. The method comprises providing a bioreactor 2 formed from a tubular vessel 4 with outer walls 24. The outer walls 24 have an inside surface and an outside surface and are constructed at least partially of a gas permeable material. The tubular vessel 4 has closed ends and a substantially horizontal longitudinal central axis extending between the ends. A means to controllably rotate the tubular vessel 4 about its substantiaily horizontal longitudinal central axis is provided. A means to introduce an oxygen-containing liquid throughout said tubular vessel is also provided.

The inside surface is coated with a material to which a plurality of cells may attach. Then the bioreactor 2 is filled with a liquid culture medium and mammalian cells. The cells are suspended, without appreciable mixing, in the liquid culture medium by rotating the bioreactor 2 about its substantially horizontal longitudinal central axis at a rate that suspends the cells in the liquid culture medium. The rate of rotation is varied such that the cells attach to the inside surface of the vessel 4. The rotation is continued for a time period that permits cell growth adjacent to the inside surface of the vessel 4. The vessel 4 is continually permeated with gas through the outer walls 24. Preferably, a constant flow of liquid culture medium is maintained in and out of the vessel 4. In a preferred embodiment, a constant flow of an oxygen rich liquid is maintained in and out of the vessel, such as fluorocarbon oils, silicone oils, or blood. In an alternative embodiment, this method may be employed with a vessel that does not have gas permeable walls.

In use, skin cells may be cultured to form a layer of skin on the inner surface of the vessel 4. Once the cells have attached and formed a complete layer of skin the vessel can be opened and the skin removed in an intact sheet. This method may also be employed using a means for attaching the cells to the inner surface that forms strings spanning the interior of the vessel 4 for the cells to attach and form three-dimensional tissue structures in vitro.

The methods of the present invention may also be used with other embodiments of the bioreactor 2 of the present invention.

Notwithstanding that the invention is described in terms of particular preferred embodiments, it will be understood that the present invention is not to be construed as limited to such, rather to the lawful scope of the appended claims.

What is claimed is:

1. A bioreactor comprising:
    a tubular vessel with outer walls having an inner surface and an outer surface, said tubular vessel having closed ends and a substantially horizontal longitudinal central axis said tubular vessel is constructed with a first half of said outer wall comprised of gas permeable material and a second half of said outer wall comprised of a non-gas permeable material;
    means for rotating said tubular vessel about said substantially horizontal longitudinal central axis; and
    two or more vessel access ports for transferring materials into and out of the tubular vessel; said inner surface further comprising a means for attaching cells.

2. A bioreactor comprising:
    a tubular vessel with outer walls having an inner surface and an outer surface, said outer walls constructed at least partially of a gas permeable material, said tubular vessel having closed ends and a substantially horizontal longitudinal central axis;
    means for rotating said tubular vessel about said substantially horizontal longitudinal central axis;
    two or more vessel access ports for transferring materials into and out of the tubular vessel; and
    a rotatable connecting means attached to said two or more vessel access port; said inner surface further comprising a means for attaching cells.

3. A method for culturing cells in a bioreactor to produce in vitro multi-cellular, three dimensional assemblies of predominately living mammalian cells attached to the inside surface of the bioreactor, said method comprising:
    providing a bioreactor formed from a tubular vessel having outer walls, said outer walls having an inside surface and an outside surface, said outer walls constructed at least partially of a gas permeable material, said tubular vessel having closed ends and a substantially horizontal longitudinal central axis extending between said ends, means to controllably rotate said tubular vessel about its substantially horizontal longitudinal central axis, means to introduce an oxygen-containing fluid throughout said tubular vessel;
    coating said inside surface with a material to which a plurality of cells may attach;
    filling said bioreactor with a liquid culture medium and mammalian cells;
    suspending said cells, without appreciable mixing, in the liquid culture medium by rotating said bioreactor about its substantially horizontal longitudinal central axis at a rate that suspends the cells in the liquid culture medium;
    varying the rate of rotation such that the cells attach to the inside surface of the vessel;
    continuing rotation of the bioreactor for a time period that permits cell growth adjacent to the inside surface of the vessel; and
    maintaining a constant flow of liquid culture medium in and out of the vessel;
    wherein gas is permeated through the outer wall of the tubular vessel.

4. A method for culturing cells in a bioreactor to produce in vitro multi-cellular, three dimensional assemblies of predominately living mammalian cells attached to the inside surface of the bioreactor, said method comprising:

providing a bioreactor formed from a tubular vessel having outer walls, said outer walls having an inside surface and an outside surface, said outer walls constructed at least partially of a gas permeable material, said tubular vessel having closed ends and a substantially horizontal longitudinal central axis extending between said ends, means to controllably rotate said tubular vessel about its substantially horizontal longitudinal central axis, means to introduce an oxygen-containing fluid throughout said tubular vessel;

coating said inside surface with a material to which a plurality of cells may attach;

filling said bioreactor with a liquid .culture medium and mammalian cells;

suspending said cells, without appreciable mixing, in the liquid culture medium by rotating said bioreactor about its substantially horizontal longitudinal central axis at a rate that suspends the cells in the liquid culture medium;

varying the rate of rotation such that the cells attach to the inside surface of the vessel; and continuing rotation of the bioreactor for a time period that permits cell growth adjacent to the inside surface of the vessel;

maintaining a constant flow of an oxygen rich liquid in and out of the vessel;

wherein gas is permeated through the outer wall of the tubular vessel.

5. The method of claim 4, wherein the oxygen rich liquid is selected from the group consisting of fluorocarbon oils, silicone oils, and blood.

6. A method for culturing cells in a bioreactor to produce in vitro multi-cellular, three dimensional assemblies of predominately living mammalian cells attached to the inside surface of the bioreactor, said method comprising:

providing a bioreactor formed from a tubular vessel having an outer wall having an inside surface and an outside surface, said tubular vessel having closed ends and a substantially horizontal longitudinal central axis extending between said ends, means to controllably rotate said tubular vessel about its substantially horizontal longitudinal central axis, means to introduce an oxygen-containing fluid throughout said tubular vessel;

coating said inside surface with a material to which a plurality of cells may attach;

filling said bioreactor with a liquid culture medium and mammalian cells;

suspending said cells, without appreciable mixing, in the liquid culture medium by rotating said bioreactor about its substantially horizontal longitudinal central axis at a rate that suspends the cells in the liquid culture medium;

varying the rate of rotation such that the cells attach to the inside surface of the vessel;

maintaining a constant flow of liquid culture medium in and out of the vessel; and continuing rotation of the bioreactor for a time period that permits cell growth adjacent to the inside surface of the vessel.

7. A method for culturing cells in a bioreactor to produce in vitro multi-cellular, three dimensional assemblies of predominately living mammalian cells attached to the inside surface of the bioreactor, said method comprising:

providing a bioreactor formed from a tubular vessel having an outer wall having an inside surface and an outside surface, said tubular vessel having closed ends and a substantially horizontal longitudinal central axis extending between said ends, means to controllably rotate said tubular vessel about its substantially horizontal longitudinal central axis, means to introduce an oxygen-containing fluid throughout said tubular vessel;

coating said inside surface with a material to which a plurality of cells may attach;

filling said bioreactor with a liquid culture medium and mammalian cells;

suspending said cells, without appreciable mixing, in the liquid culture medium by rotating said bioreactor about its substantially horizontal longitudinal central axis at a rate that suspends the cells in the liquid culture medium;

varying the rate of rotation such that the cells attach to the inside surface of the vessel;

maintaining a constant flow of an oxygen rich liquid in and out of the vessel; and continuing rotation of the bioreactor for a time period that permits cell growth adjacent to the inside surface of the vessel.

8. The method of claim 7, wherein the oxygen rich liquid is selected from the group consisting of fluorocarbon oils, silicone oils, and blood.

* * * * *